(12) United States Patent  
Oderwald et al.

(10) Patent No.: US 9,138,135 B2
(45) Date of Patent: Sep. 22, 2015

(54) SYSTEM, A METHOD AND A COMPUTER PROGRAM FOR INSPECTION OF A THREE-DIMENSIONAL ENVIRONMENT BY A USER

(75) Inventors: Michiel Peter Oderwald, Delft (NL); Fokko Pieter Wieringa, Elst (NL)

(73) Assignee: NEDERLANDSE ORGANISATIE VOOR TOEGEPAST-NATUURWETENSCHAPPELIJK ONDERZOEK TNO, Delft (NL)

(*) Notice: Subject to any disclaimer, the term of this patent is extended or adjusted under 35 U.S.C. 154(b) by 1087 days.

(21) Appl. No.: 13/054,360

(22) PCT Filed: Jul. 17, 2009

(86) PCT No.: PCT/NL2009/050444
§ 371 (c)(1),
(2), (4) Date: Apr. 21, 2011

(87) PCT Pub. No.: WO2010/008292
PCT Pub. Date: Jan. 21, 2010

(65) Prior Publication Data
US 2011/0193938 A1    Aug. 11, 2011

(30) Foreign Application Priority Data

Jul. 17, 2008  (EP) .................................... 08160646

(51) Int. Cl.
*H04N 13/00* (2006.01)
*A61B 1/05* (2006.01)
*A61B 1/00* (2006.01)

(52) U.S. Cl.
CPC ............... *A61B 1/05* (2013.01); *A61B 1/00045* (2013.01); *A61B 1/00181* (2013.01); *A61B 1/00183* (2013.01)

(58) Field of Classification Search
CPC ........... A61B 1/00045; A61B 1/00181; A61B 1/00183; A61B 1/05
USPC .............................................. 348/45, E13.074
See application file for complete search history.

(56) References Cited

U.S. PATENT DOCUMENTS 5,381,784 A    1/1995   Adair
5,776,050 A *  7/1998   Chen et al. .................... 600/117
(Continued)

FOREIGN PATENT DOCUMENTS

JP    63-274911 A    11/1988
JP     2-55907 A     2/1990
(Continued)

*Primary Examiner* — Christopher S Kelley
*Assistant Examiner* — Asmamaw G Tarko
(74) *Attorney, Agent, or Firm* — Leydig, Voit & Mayer, Ltd.

(57) ABSTRACT

A system for inspection of a three-dimensional environment by a user may include a tool arranged to be introduced in a vicinity of the three-dimensional environment, the tool including one or more cameras arranged at or near a distal end of the tool, the one or more cameras arranged to generate respective images of the three-dimensional environment; a display unit arranged to receive said respective images; and a motion tracking system arranged to determine a position of at least a portion of the user for selecting an image generated by the cameras or for causing the one or more cameras to generate the image on demand and for displaying the image on the display. A method, a tool, and a display unit for enabling inspection of an object by a user, as well as use of a tool, may include at least one camera in the system as set forth in the foregoing.

10 Claims, 9 Drawing Sheets

(56) References Cited

U.S. PATENT DOCUMENTS

| | | | |
|---|---|---|---|
| 6,292,221 B1 | 9/2001 | Lichtman | |
| 6,652,452 B1 | 11/2003 | Seifert et al. | |
| 7,636,200 B2* | 12/2009 | Ishibashi et al. | 359/634 |
| 2002/0131734 A1 | 9/2002 | Stark | |
| 2002/0183727 A1 | 12/2002 | Daikuzono | |
| 2003/0234940 A1 | 12/2003 | Farr et al. | |
| 2005/0089212 A1* | 4/2005 | Mashitani et al. | 382/154 |
| 2009/0102916 A1* | 4/2009 | Saishu et al. | 348/54 |
| 2009/0219224 A1* | 9/2009 | Elg | 345/8 |
| 2010/0053151 A1* | 3/2010 | Marti et al. | 345/419 |
| 2010/0231688 A1* | 9/2010 | Park et al. | 348/42 |
| 2011/0007262 A1* | 1/2011 | Taylor et al. | 351/60 |
| 2011/0137156 A1* | 6/2011 | Razzaque et al. | 600/424 |
| 2011/0157174 A1* | 6/2011 | Mashitani et al. | 345/419 |
| 2011/0157319 A1* | 6/2011 | Mashitani et al. | 348/49 |
| 2011/0194065 A1* | 8/2011 | Belbey et al. | 351/60 |
| 2012/0038635 A1* | 2/2012 | Stamate et al. | 345/419 |
| 2012/0044249 A1* | 2/2012 | Mashitani et al. | 345/419 |
| 2012/0155731 A1* | 6/2012 | Weersink et al. | 382/131 |
| 2013/0225078 A1* | 8/2013 | Johansson et al. | 455/41.2 |

FOREIGN PATENT DOCUMENTS

| | | |
|---|---|---|
| JP | 2-55907 U | 4/1990 |
| JP | 6-59196 A | 3/1994 |
| JP | 7-296139 A | 11/1995 |
| JP | 8-237687 A | 9/1996 |

* cited by examiner

SYSTEM, A METHOD AND A COMPUTER PROGRAM FOR INSPECTION OF A THREE-DIMENSIONAL ENVIRONMENT BY A USER

CROSS-REFERENCE TO RELATED APPLICATIONS

This application is filed under 35 U.S.C. 371 as a U.S. national phase application of PCT/NL2009/050444, having an international filing date of 17 Jul. 2009, which claims the benefit of European Patent Application No. 08160646.9, having a filing date of 17 Jul. 2008, both of which are hereby incorporated by reference.

FIELD OF THE INVENTION

The invention relates to a system for inspection of a three-dimensional environment by a user. In particular, the invention relates to a system for inspecting a target area during endoscopic operation.

The invention further relates to a method for enabling inspection of a three-dimensional environment by a user.

The invention still further relates to a tool and a display unit for use in the system as is set forth in the foregoing.

The invention still further relates to use of a tool in the system as is set forth in the foregoing.

BACKGROUND OF THE INVENTION

An embodiment of a system for inspection of a three-dimensional environment is known in the art of endoscopic operations, in particular in the art of minimally invasive endoscopic operations, wherein a stereo-endoscope is used. In this case a surgeon has to wear special glasses or a head-mounted device for enabling him to perceive an inspected target area in three-dimensions.

It is a disadvantage of the known system that the surgeon has to wear additional equipment during implementation of an operative intervention, which may hinder him.

SUMMARY OF THE INVENTION

It may be desirable to provide a system for inspection of a three-dimensional environment, which enables three-dimensional perception of a suitable three-dimensional environment comprising an object, a feature or a combination of both, while causing no worsening of a comfort of the user.

To this end the system according to the invention comprises:
- a tool arranged to be introduced in a vicinity of the three-dimensional environment, said tool comprising at least one camera chip arranged to generate a plurality of images of objects present in the three-dimensional environment, said plurality of images having respective viewpoints;
- a display unit arranged to receive at least one image from said plurality of images;
- a motion tracking system arranged to determine a viewing position of the user for selecting or for generating an image from the said at least one camera chip for displaying said image on the display, wherein said image has a viewpoint corresponding to the said viewing position.

In particular, the system according to the invention relates to a system for enabling three-dimensional viewing, for example during minimally invasive operation, wherein for the tool an endoscope is used. In this case the one or more camera chips may be arranged on a distal portion of the endoscope. The system according to the invention enhances natural coupling between visual input and proprioception by offering views from different angles controlled by the position of the viewer's eyes or head. It will be appreciated that such offering may be enabled either by controlling a spatial position and/or orientation of the at least one camera chip followed by generation of an image with a required viewpoint, or by selecting a suitable image from a plurality of generated images. In particular, the step of selecting may comprise a step of interpolating between generated images for obtaining an image accurately matching required viewpoint.

It will be appreciated that the term 'at least one camera chip' may relate to a sole camera chip or an array or a matrix of camera chips. It will further be appreciated that the term 'object' may either relate to suitable bodies present in the three-dimensional environment, or to suitable two-dimensional or three-dimensional structures. It will still further be appreciated that the operation of the system according to the invention may be defined with respect to a plurality of coordinate systems. For example, a coordinate system related to the three-dimensional environment may be selected as a starting point, wherein the display screen and/or images of the three-dimensional environment may be assigned respective coordinates. In this case, the motion tracking system may be arranged to determine a viewing position of the viewer in the coordinate system of the three-dimensional environment. Alternatively, the three-dimensional environment may be assigned to a first coordinate system, the display unit may be assigned to a second coordinate system, which is related by suitable transformation with the first coordinate system. The motion tracking system can then be arranged to determine the viewing position of the user with respect to the display unit where after a suitable image is selected or is generated. Still alternatively, the system according to the invention may be operable in the world coordinate system, wherein the three-dimensional environment, the display unit, the motion tracking system and the user are characterized in the world coordinate system. It will be apparent to those in the art that a plurality of suitable modifications regarding the choice of one or more coordinate systems and operation of the motion tracking system therein is possible without departing from the invention.

The technical measure of the invention is based on the insight that by providing suitable tracking of a position of, for example, eyes or a face of the user and by providing an image to the user corresponding to his position, and thus, his viewpoint a movement parallax can be simulated on the display. As a result, enhancement of a three-dimensional perception of the user of spatial interrelations regarding inspected three-dimensional environment is improved. In particular, spatial relationship between occluded object portions and/or further objects in the three-dimensional environment is made clearly perceptible. In particular, depth perception is enhanced.

In particular, for minimally invasive surgery the system according to the invention provides substantial improvement of spatial orientation of the surgeon as he or she is not limited to two-dimensional images as provided by a single camera on one hand, and is not hindered by a necessity to wear additional glasses or a head-mounted device, on the other hand. Additionally, the system improves depth perception by enhancing the match between proprioceptional input (i.e. movement of head and eyes) and the resulting visual input.

It will be appreciated that in the system according to the invention per se known endoscopes may be used. A first type of endoscopes as known in the art may comprise a multiple lens system cooperating with one or two camera chips for obtaining one or two images of a three-dimensional environment inside a human body. Next, a stereo-endoscope may be used for providing two images on one or two camera chips.

Alternatively, it is also possible that a camera chip is arranged with a single lens, said camera chip and said lens being translatable and rotatable together as a unit. Additionally, it is possible to introduce a plurality of endoscopes, for example 2, 3, or more via different entry points (trocards) and allow the user to switch between the respective different images produced by one or more camera chips arranged on these endoscopes using head motion.

In an embodiment of the system according to the invention the at least one camera chip is displaceable for generating the plurality of images having respective viewpoints.

It is found to be advantageous to arrange the at least one camera chip displaceably with respect to the tool. It will be appreciated that either a sole camera chip may be displaceable, or a plurality of camera chips may be displaceable. In the former case, the camera chip may be arranged either to generate a sole image over its length or it may be arranged with a plurality of sub-regions for generation a corresponding plurality of images over its length. In case when an area of the camera chip is divided into sub-regions operating individually, the camera chip may be provided with a multi-lens structure for cooperating with said sub-regions. In this way generation of a plurality of images may be enabled. It will be appreciated that such individual images may still be combined for yielding a combined seamless image by cumulatively appending individual images. Preferably, a light barrier for optically separating said sub-regions is provided. In this way optical cross-talk between sub-regions is reduced. It will be appreciated that the term 'displaceable' relates not only to lateral displacement but also to a rotational displacement. Preferably, an angle of the at least one camera chip is controllable. This feature is particularly useful for a plurality of camera chips, as a degree of concentricity of the camera chips may by controllable for enabling focusing of the camera chips either on a proximal or a distal object present in the inspected three-dimensional environment.

Preferably, the at least one camera chip is motorized for enabling displacement with respect to the tool. Alternatively, or additionally the at least one camera chip may be arranged on a support, the support being displaceable with respect to the tool.

In a further embodiment of the system according to the invention the motion tracking system is further arranged to control a displacement of the at least one camera chip for generating said image having said viewpoint.

It is possible that in the system according to the invention the motion tracking system is arranged to generate a trigger signal for causing the camera chip or the camera chips to displace. For example, the trigger signal may be sent to a servo motor cooperating with the camera chip or the camera chips and causing their corresponding displacement. Alternatively, the trigger signal may be sent to a displaceable support causing movement thereof for enabling the camera chip or the camera chips to take an image from desired viewpoint or viewpoints. Use of an array or a matrix may be advantageous when one or more images are to be selected from previously generated images. In this embodiment, it is possible to generate images of the three-dimensional environment by the individual camera chips and to subsequently store them. The user may control selection of a suitable image from the stored images by his head motion. In this case a system response may be higher than the system response obtainable from a displaceable single camera chip. It will be appreciated that this embodiment may be useful for inspecting of a substantially static three-dimensional environment. In practice, in particular, during medical interventions, it is preferable to generate a suitable image on demand, said demand being controllable by a change of a user's viewing position.

When equipping the tool with a displaceable camera chip or displaceable camera chips, the system according to the invention may be arranged to, first, detect a dwell position of a portion of the user, for example of its eyes or a face and then to displace the camera chip or the camera chips in such a way that these camera chip or camera chips generate an image or images of the three-dimensional environment having the same viewpoint as a virtual viewpoint corresponding to the dwell position of the user. In this way instead of selecting an image from a plurality of generated images a generation of an on-demand image is performed, which may be advantageous in term of the system response time.

It will be appreciated that it is possible to provide the toll with a sole camera chip which is divided into sub-regions, each sub-region being capable of generating an individual image. In this way a plurality of camera chips is provided. It may be possible to use such plurality of sub-regions as individual sources of images, or, if required, to electronically combine them for generation of a single image using substantially the whole area of the chip. Preferably, a multi-lens structure is provided for cooperating with said sub-regions in order to enable generation of individual images. In order to reduce optical cross-talk between the sub-regions, the tool may be provided with a light barrier for optically separating said sub-regions.

In an embodiment of the system according to the invention the array of cameras is arranged concentrically.

It is found to be particularly advantageous to provide a substantially equidistant array of cameras with respect to the three-dimensional environment. In particular, in the field of minimally invasive surgery it is found to be preferable to avoid intra-image distortion due to difference in respective distances of the camera chips to the said object. This may be achieved by arranging said camera chips concentrically, for example, on a concentric line. This may be achieved, for example by arranging optical axes of the camera chips aimed at one mutual point in the three-dimensional environment. In case when a matrix of camera chips is used, said camera chips may be arranged on e.g. a concentric, or parabolic area provided on the distal portion of the endoscope, preferably on its tip. Alternatively, or additionally the camera chips may be arranged with an increasing degree of rotation about their individual axes as a function of a displacement of the camera chip with respect to the center line of the endoscope. In this case a support on which the camera chips are arranged may be kept straight. It will be appreciated that other spatial arrangement of the camera chips is possible, for example ex-centric, parallel, outward looking panoramic, etc.

It will be further appreciated that respective angles of the camera chips may be adjustable yielding an adjustable degree of concentricity of the array or the matrix of the camera chips. This has an advantage that a position of the mutual focus is adjustable, in particular that a depth position of the mutual focus is adjustable.

In a further embodiment of the system according to the invention, said at least a portion of the user comprises a face or eyes.

It will be appreciated that substantially any of the known motion tracking systems may be used in the system according to the invention. However, it may be preferable, particularly in the field of minimally invasive surgery to arrange the motion tracking system to detect a displacement of a head, or face, or eyes of the user and to select an image from said plurality of cameras in accordance with said displacement. The displacement may be suitably determined by a camera-based system, wherein the camera of the motion tracking system may be positioned on or nearby a display whereon the images of a suitable object from the inspected three-dimensional environment are projected. In order to minimize the hassle for user, a suitable head tracking system may be arranged to function without a need for the user to wear special glasses, sensors or markers. This embodiment will be explained in more detail with reference to FIGS. 1 and 2. It will be appreciated that the motion tracking system may be based on a suitable plurality of available technologies, comprising, but not limited to camera-based systems, magnetic/RF motion tracking systems, etc.

In a still further embodiment of the system according to the invention it further comprises a control unit arranged to select two images of the said plurality of images for displaying a stereoscopic image with parallax on the display for a position of the user, said stereoscopic image corresponding to said position.

It is found advantageous to provide more than one image at a time for viewing, thereby enabling stereoscopic viewing mode by the user. The stereoscopic viewing mode may be supported by equipping the user with stereoscopic glasses, or, alternatively by projecting the selected images on a dedicated display arranged to enable a three-dimensional viewing.

In a still further embodiment of the system according to the invention, the system further comprises a processing unit for reconstructing intermediate images interpolating between the said plurality of images.

It is found to be advantageous in a system comprising a plurality of camera chips, which may be arranged in an array or in a matrix, to interpolate between individual images taken by individual camera chips. It will be clear for a skilled artisan that interpolating images can also be calculated from the distinct positions in order to smooth irregularities between discrete images taken at different viewing positions. Methods for interpolating between images are known from the art, for example per se known 3D interpolation may be used, based, for example on disparity estimation algorithm. It will be appreciated that other algorithms known for interpolating between images may be applied. This functionality enables a smooth interface between individual images taken of the three-dimensional environment, which eases comprehension thereof by the user.

A method according to the invention for enabling inspection of a three-dimensional environment by a user, comprises:
  generating a plurality of images of the three-dimensional environment from a plurality of different viewpoints;
  tracking viewing position of the user for selecting an image from said plurality of images or for generating an image, said image having a viewpoint corresponding to said viewing position;
  displaying the image corresponding to the viewpoint on a display.

In particular, the said plurality of different views may be generated by a tool provided with a camera chip or an array or a matrix of cameras at or near its distal portion. In a more particular embodiment the tool relates to an endoscopic apparatus.

A computer program product according to the invention for enabling inspection of a three-dimensional environment by a user comprises instructions for causing a processor to carry out steps of the method as is set forth in the foregoing.

A tool for use in a system according to the invention comprises at least one camera chip arranged at or near a distal end of the tool. In particular, the tool according to the invention relates to an endoscope provided with one or more camera chips arranged on or near a distal portion of the endoscope.

A display unit according to the invention comprises:
  a display;
  a motion tracking system for determining a viewing position of a user with respect to a three-dimensional environment conceived to be inspected;
  a control system arranged to receive information about said viewing position of the portion of the user and to generate a trigger signal to cause an image source to select or to generate an image having a viewpoint corresponding to the said viewing position.

The invention further relates to the use of a tool comprising an array of cameras arranged at or near a distal end of a tool for providing a plurality of images in a system as is described in the foregoing.

The invention still further relates to the use of a tool comprising at least one camera arranged at or near a distal end of the tool for providing a plurality of images having different viewpoints in a system as is set forth in the foregoing. Preferably, for the tool an endoscope is selected.

These and other aspects of the invention will be discussed in more detail with reference to drawings, wherein like reference signs relate to like elements. It will be appreciated that the drawings are presented for illustrative purposes only and may not be used for limiting the scope of the appended claims.

DETAILED DESCRIPTION OF THE DRAWINGS

Figure 1:
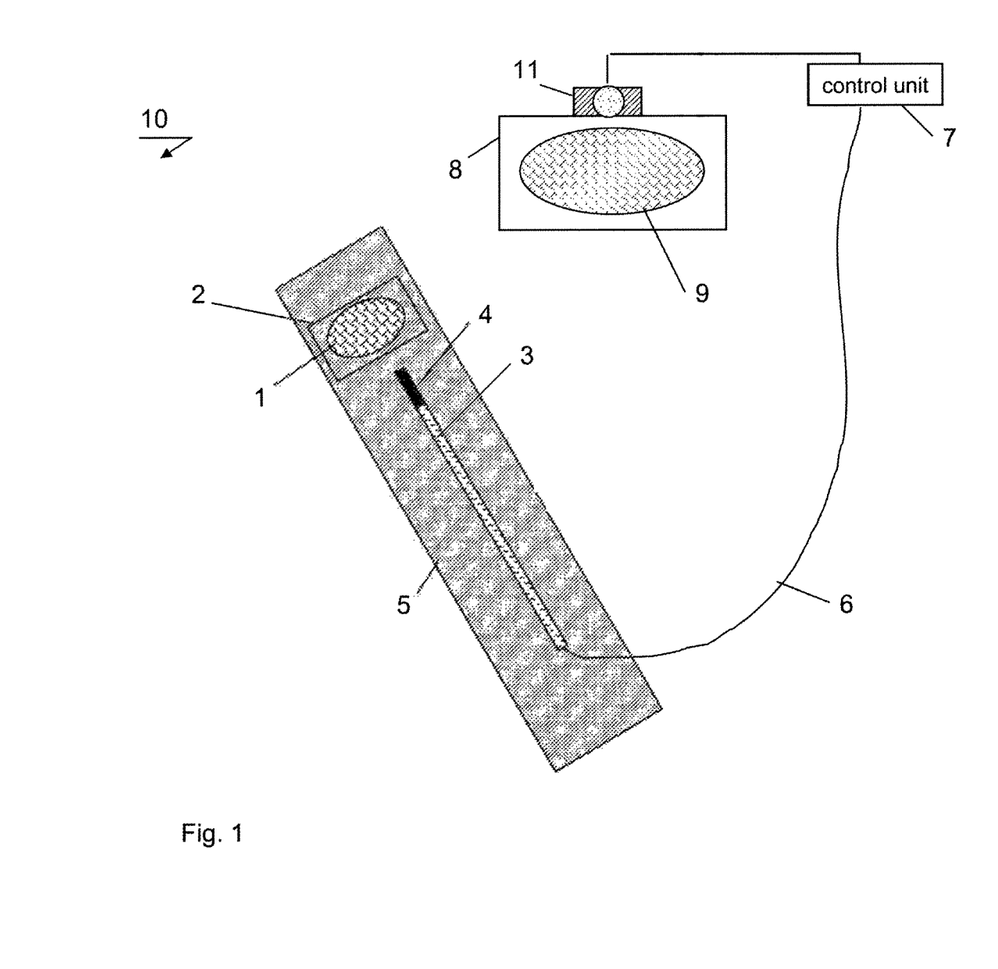
FIG. 1 presents a schematic view of an embodiment of a system according to the invention.

FIG. 1 presents a schematic view of an embodiment of a system according to the invention. The system 10 comprises a tool 3 provided with an array of cameras 4 arranged on a distal portion 4 of the tool 3 for inspecting an object 1, for example a hidden object, which may relate to a target area within a patient 2. For ease of the inspection the patient 2 may be positioned on a support table 5. The system 10 further comprises a display 8 conceived to display an image 9 from one of the cameras from said plurality of cameras arranged on the tool 3. In order to enable a proper selection of the camera which image is to be projected on the display 8, the system 10 further comprises a motion tracking system 11 adapted to determine a viewing position of a user, for example, with respect to the object 1 or the motion tracking system 11. Preferably, the motion tracking system 11 is camera-based and is provided with a suitable image processor for detecting a portion of the user (not shown) to be traced and for detecting any displacement of the portion of the user in time. Any state of the art motion tracking system may be used for the motion tracking system, 11. In particular, motion tracking system may be arranged for detecting a face of a user using an imaging device and to track suitable points of interest on the face. Nose, chin or the like may be used for points of interest. Additionally or alternatively, the motion tracking system 11 may be arranged to detect eyes of the user and to motion track any displacement of the eyes irrespective of the displacement of the face. This embodiment is particularly useful when a different viewing angle is enabled by the user merely by displacing his eyes.

The system 10 according to the invention further comprises a control unit 7, which may be arranged in connection with the tool 3 for selecting a camera from said plurality of cameras pursuant to detected displacement of the user. The control unit 7 may then be arranged to feed the image from the selected camera on the display 9. The control unit 7 may be further arranged to cause a suitable displacement of the cameras pursuant to a detected motion of the user. As a result, the user is provided with a motion parallax simulating system, wherein a sequence of two-dimensional images from the tool 3 is provided on the display 8 in consequence to a change of the viewing angle of the viewer. In this way an improved quasi three-dimensional visualization of the object and/or its surroundings is enabled. More details on motion parallax will be discussed with reference to FIG. 4.

Figure 2:
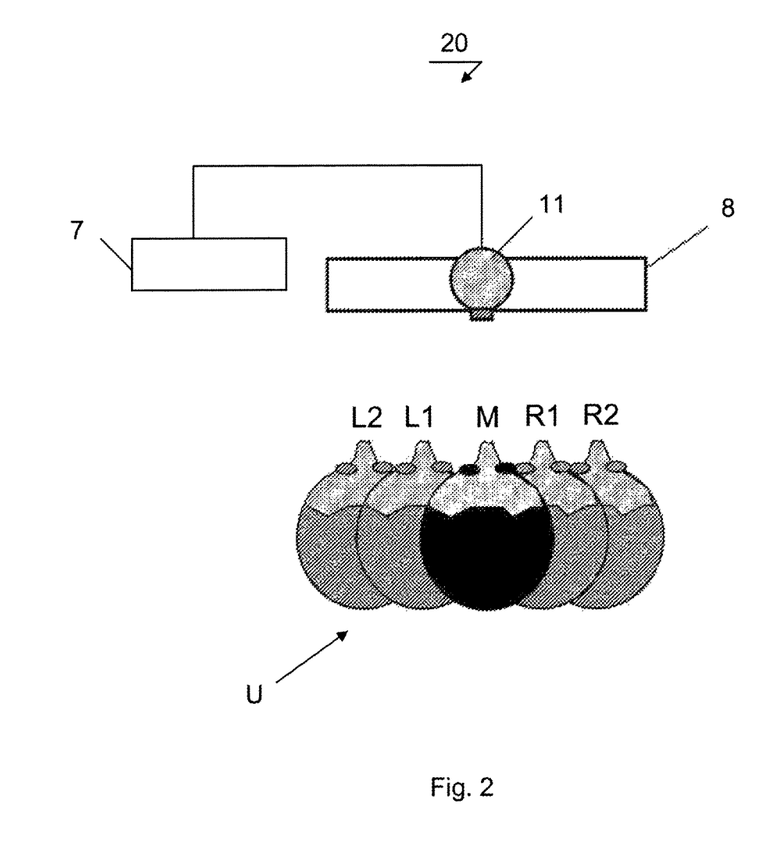
FIG. 2 present a schematic view of an embodiment of a display for use in the system of FIG. 1.

FIG. 2 present a schematic view 20 of an embodiment of a display for use in the system of FIG. 1. The display 8 may be provided with a stationary camera 11, which is in connection to the control unit 7, discussed with reference to FIG. 1. A user's head, schematically indicated by U, may first take a position, schematically labeled as a median position M. The control unit 7 may be arranged to feed an image from a central camera of the tool (not shown) to the display 8. Such initial frontal imaging may be advantageous for positioning the tool in a vicinity of the three-dimensional environment, for example during insertion of an endoscope equipped with a camera array inside a patient. When the user U has properly positioned the tool, he may displace his head in a left-right direction, schematically indicated by L2, L1, R1, R2 for simulating movement parallax on the display 8. The movement parallax will appear as a sequence of images from individual cameras of the camera array, wherein each individual image corresponds to a respective camera positioned left or right with respect to a central camera. It will be appreciated that, alternatively, the motion parallax may be enabled by suitably displacing one or more cameras. It will further be appreciated that although operation of the system according to the invention is discussed with reference to a plurality of cameras arranged at or near the distal portion of the tool, use of at least two cameras is sufficient for reaching such effect. Alternatively or additionally the cameras and/or camera support may be motorized to displace the cameras with respect to the tool. This embodiment is discussed in more detail with reference to FIG. 3.

Figure 3:
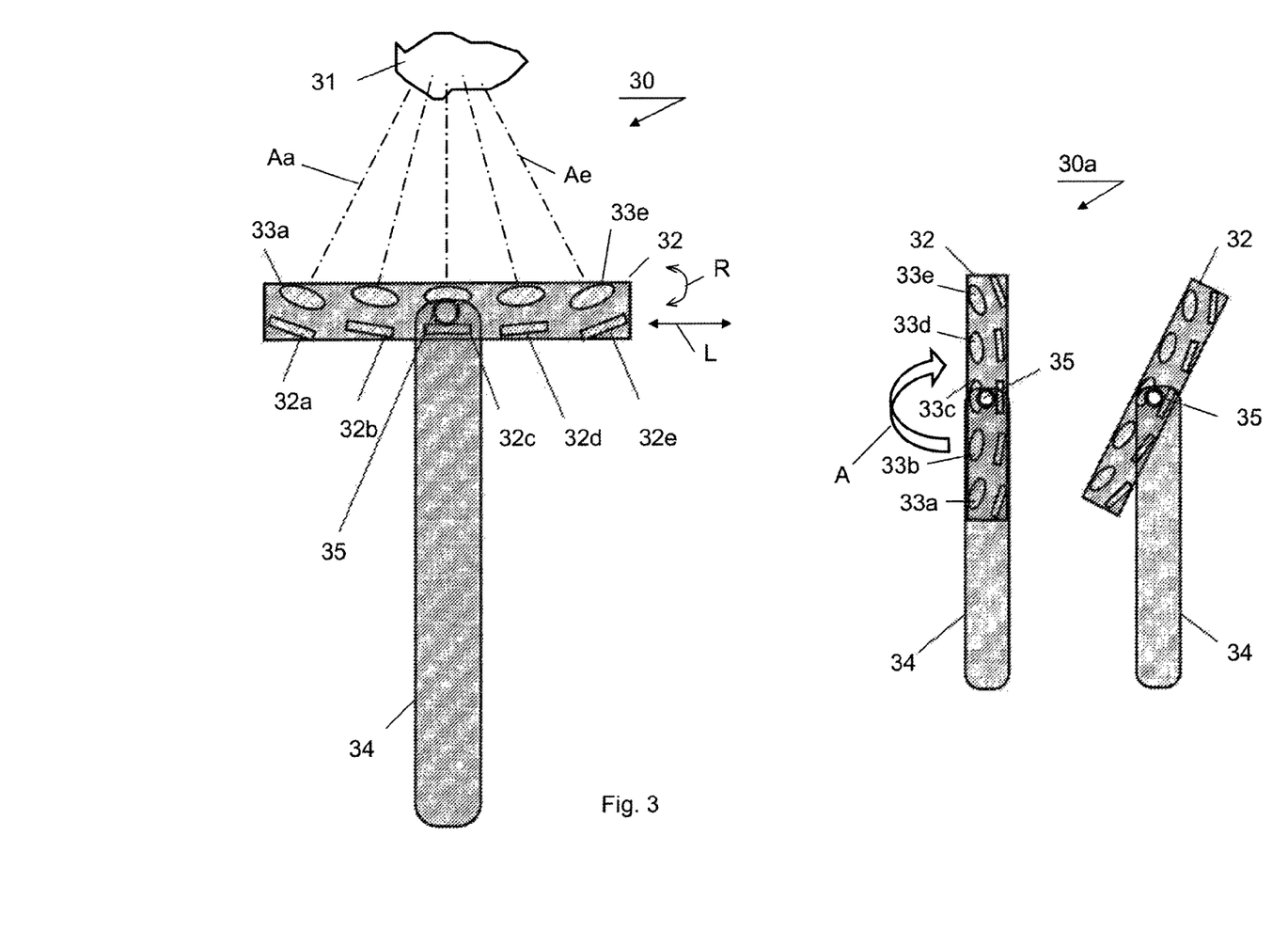
FIG. 3 present a schematic view of an embodiment of a tool in the system of FIG. 1.

FIG. 3 presents a schematic view of an embodiment of a tool for use in the system of FIG. 1. The tool 30 may relate to any object, in particular, the tool 30 may relate to an endoscopic device provided with a body 34 having a distal portion whereat a support 32 provided with a plurality cameras 32*a*, 32*b*, 32*c*, 32*d*, 32*e* may be arranged. Each camera 32*a*, 32*b*, 32*c*, 32*d*, 32*e* may be provided with an individual lens 33*a*, . . . , 33*e* for focusing an image of a three-dimensional environment 31 on respective cameras. The support may be pivotably arranged, using a pivot 35, with respect to the body 34 for enabling suitable rotation of the support 21 with respect to the body, as is schematically indicated by the arrow A in the view 30*a*. Such rotation is advantageous as off-center views may be generated, still further improving simulated three-dimensional viewing mode provided by the system according to the invention. An additional advantage of a rotating mode is a possibility in an operative setting, to provide an instrument using a right hand via a trocar. Additionally, or alternatively, the cameras 32*a*, 32*b*, 32*c*, 32*d*, 32*e* may be motorized for enabling a lateral displacement (L) and/or rotating displacement (R) of the individual cameras. As a result a set of viewing directions Aa, . . . , Ae for these cameras is enabled. By combining a lateral displacement of the camera chips 32*a*, 32*b*, 32*c*, 32*d*, 32*e* with their rotation about rotation axis, preferably perpendicular to the viewing directions Aa, . . . , Ae, the following advantageous effects may be obtained. First, the concentricity of the camera array may be adjusted allowing for focusing on a proximal or on a distal feature. Secondly, a degree of parallax may be adjusted. Thirdly, the cameras may enable displacement of a mutual focus in the vertical direction. It will be appreciated that in order to minimize internal scattering of light in the tool, the camera chips may be separated by a suitable optical barrier which may additionally play a role of a collimator.

Figure 4:
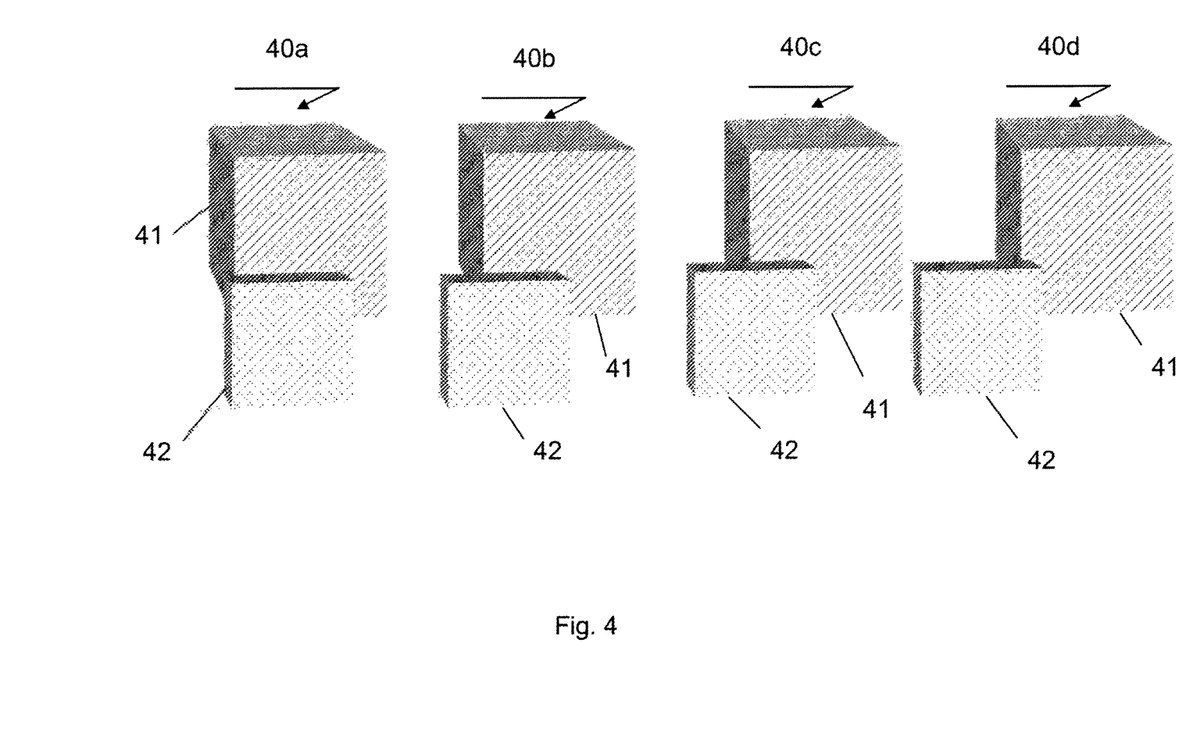
FIG. 4 presents schematically an illustration of a visualization of a movement parallax obtained with the system of FIG. 1.

FIG. 4 presents schematically an illustration of a visualization of a movement parallax obtained with the system of FIG. 1, wherein a suitable plurality of views 40*a*, 40*b*, 40*c*, 40*d* is schematically depicted. In these views movement parallax between objects 42 and 41 is demonstrated, each view 40*a*, 40*b*, 40*c*, 40*d* corresponding to a camera of the camera array as discussed with reference to FIG. 3. It is seen, that spatial interrelation between objects 41 and 42 becomes clear when a plurality of two-dimensional images of the objects 41, 42 is presented as a sequence in dependence to a viewing direction. In this drawing viewing results while moving along a line are shown. It is clear that a matrix of camera chips may be used so that the user viewpoint can be moved left, right, upwards and downwards.

Figure 5:
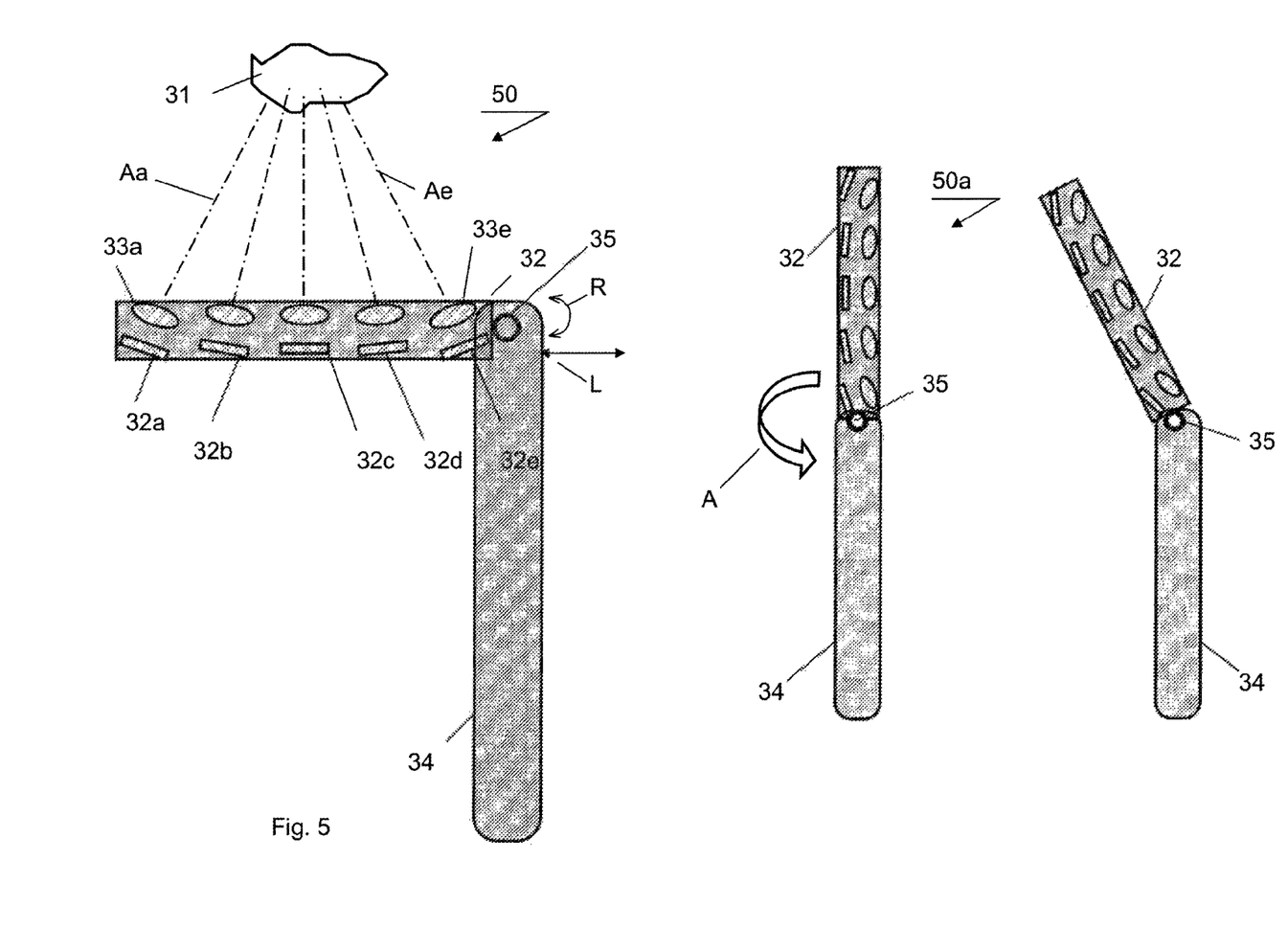
FIG. 5 presents a schematic view of a further embodiment of the tool according to the invention.

FIG. 5 presents a schematic view of a further embodiment of the tool according to the invention. The tool 50 comprises support 32 provided with a plurality cameras 32*a*, 32*b*, 32*c*, 32*d*, 32*e*. Each camera 32*a*, 32*b*, 32*c*, 32*d*, 32*e* may be provided with an individual lens 33*a*, . . . , 33*e* for focusing an image of a three-dimensional environment 31 on respective cameras. Each lens preferably forms a unit with a camera chip it cooperates with, so that any displacement of the camera chip is followed by its dedicated lens. In particular, angular displacement for altering a depth of a focus of the multi-lens system 32*a*, 32*b*, . . . , 32*e* is envisaged, allowing for inspecting proximal or distal object present in the three-dimensional environment under investigation. The support may be pivotably arranged with respect to the body 34 for enabling suitable rotation of the support 21 with respect to the body, as is schematically indicated by the arrow A in the view 50*a*. The pivot point 35 may be arranged at a suitable edge of the support 32. Preferably, at least 90 degree rotation of the support 32 is enabled. Such rotation is advantageous as off-center views may be generated, still further improving simulated three-dimensional viewing mode provided by the system according to the invention. In an operative setting the tool may be introduced from a right hand side using a trocar, which may be advantageous. Additionally, or alternatively, the cameras 32*a*, 32*b*, 32*c*, 32*d*, 32*e* may be motorized for enabling a lateral displacement (L) and/or rotating displacement (R) of the individual cameras about their axes Aa, . . . , Ae.

Figure 6:
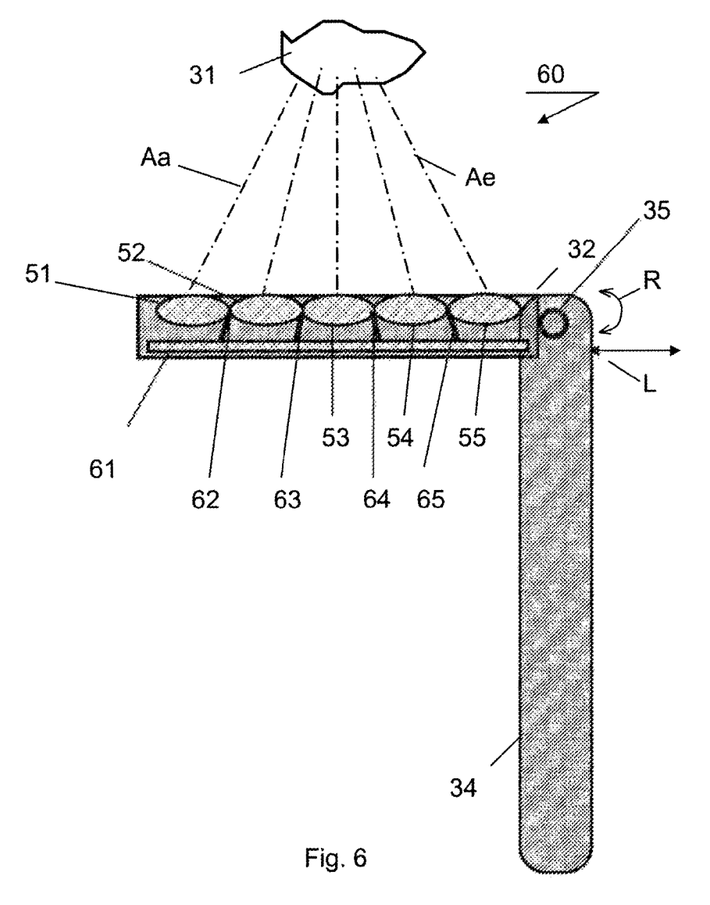
FIG. 6 presents a schematic view of a further embodiment of the tool comprising an optical barrier.

FIG. 6 presents a schematic view of a further embodiment of the tool comprising an optical barrier. The tool 60 may comprise a single camera chip 61 which may be electronically divided into sub-regions, each sub-region cooperating with its own lens 51, 52, 53, 54, 55. Alternatively, a multi-lens array may be provided, which is suitably aligned with the regions of the camera chip 61. In order to avoid optical cross-talk between the sub-regions of the camera chip, the tool 60 comprises an optical barrier 62, 64, 64, 65 optically separating the sub-regions. Further elements of the tool 60 may be kept the same, as discussed with reference to FIG. 3 or FIG. 5.

Figure 7:
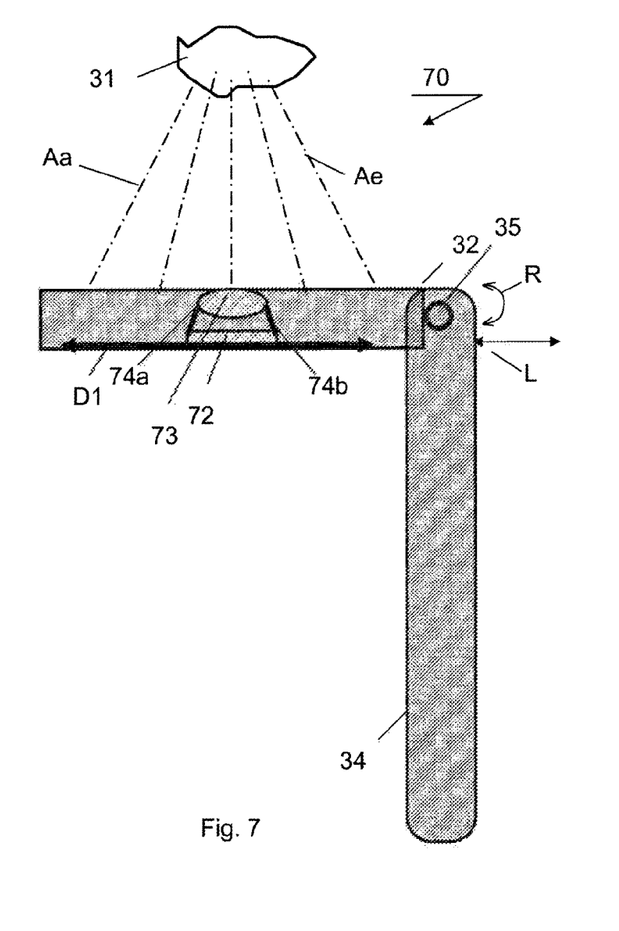
FIG. 7 presents a schematic view of a still further embodiment of the tool comprising a single displaceable camera chip.

FIG. 7 presents a schematic view of a still further embodiment of the tool comprising a single displaceable camera chip. In this particular embodiment the tool 70 is provided with a unit comprising single camera chip 72 provided with a lens 73, said unit being translatable along the support 32. The unit may be provided with optical barriers 74a, 74b for collimating the view of the camera chip on a three-dimensional environment to be inspected. Additionally or alternatively, the optical barrier prevents light photons undergone internal scattering to enter respective camera chips. Accordingly, when a position detection system (not shown) determines a current dwell position of the user, which corresponds to a viewing position, a control unit (not shown) provide a trigger signal to the unit causing lateral translation thereof to a desired position simulating viewing position of the three-dimensional environment as experienced by the user. For this purpose, the trigger signal may be applied to a suitable servo motor (not shown), which translates the unit along direction D1. Further elements shown in this figure may be the same, as discussed with reference to FIG. 3. Alternatively, it is possible that the unit is being continuously translated or translated on demand for generating a plurality of images, one or more of them to be selectable, for example, from a memory, by a control unit (not shown) of the system according to the invention for meeting a viewing direction as experienced by the user. If required, it is possible to interpolate between the generated images for accurately meeting the viewing position as experienced by the user.

Figure 8:
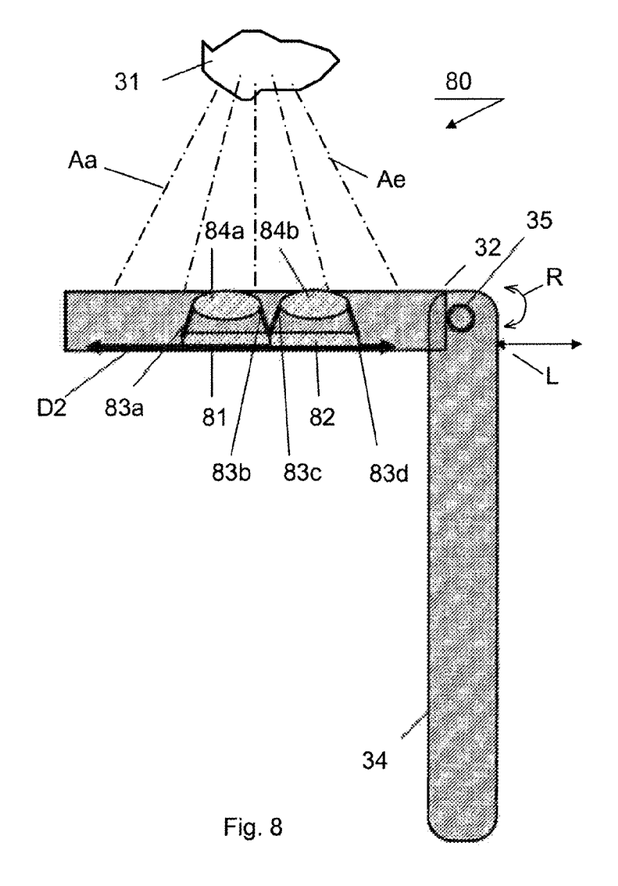
FIG. 8 presents a schematic view of a still further embodiment of the tool comprising a pair of displaceable camera chips.

FIG. 8 presents a schematic view of a still further embodiment of the tool comprising a pair of displaceable camera chips. The tool 80 may comprise a support 32, as is discussed with reference to the foregoing, which is provided with a pair of camera chips 81a, 81b, each equipped with a dedicated lens 84a, 84b, respectively. The pair is translatable along direction D2. Also, in this embodiment each camera chip may be provided with an optical barrier 83a, 83b, 83c, 83d for collimating a view of the camera chip towards a three-dimensional environment to be inspected. Additionally or alternatively, the optical barrier prevents light photons undergone internal scattering to enter respective camera chips. Also in this embodiment two alternative operational modes are possible. First, it is possible to initially detect a viewing position of the user and then to suitably translate the pair for generating an image and then to translate the pair meeting such position. Preferably, the system according to the invention comprises a three-dimensional display for displaying the images from the pair as a stereoscopic image. Alternatively, the images from the left and the right camera chip may be displayed on a conventional display and the user may wear stereoscopic glasses for enabling stereoscopic viewing.

Secondly, it is possible to continuously or on demand translate the pair along substantially the whole range within the support 32 and then, when a dwell viewing position of the user is detected, to select a suitable pair of images from already generated images, which may be suitably stored. It is also possible that the stored pairs of images are interpolated before or after retrieval for enabling accurate positional matching between the viewing position of the user and the viewing directions provided by the tool. It will be appreciated that further elements shown in FIG. 8 may be the same as discussed with reference to the foregoing Figures.

Figure 9:
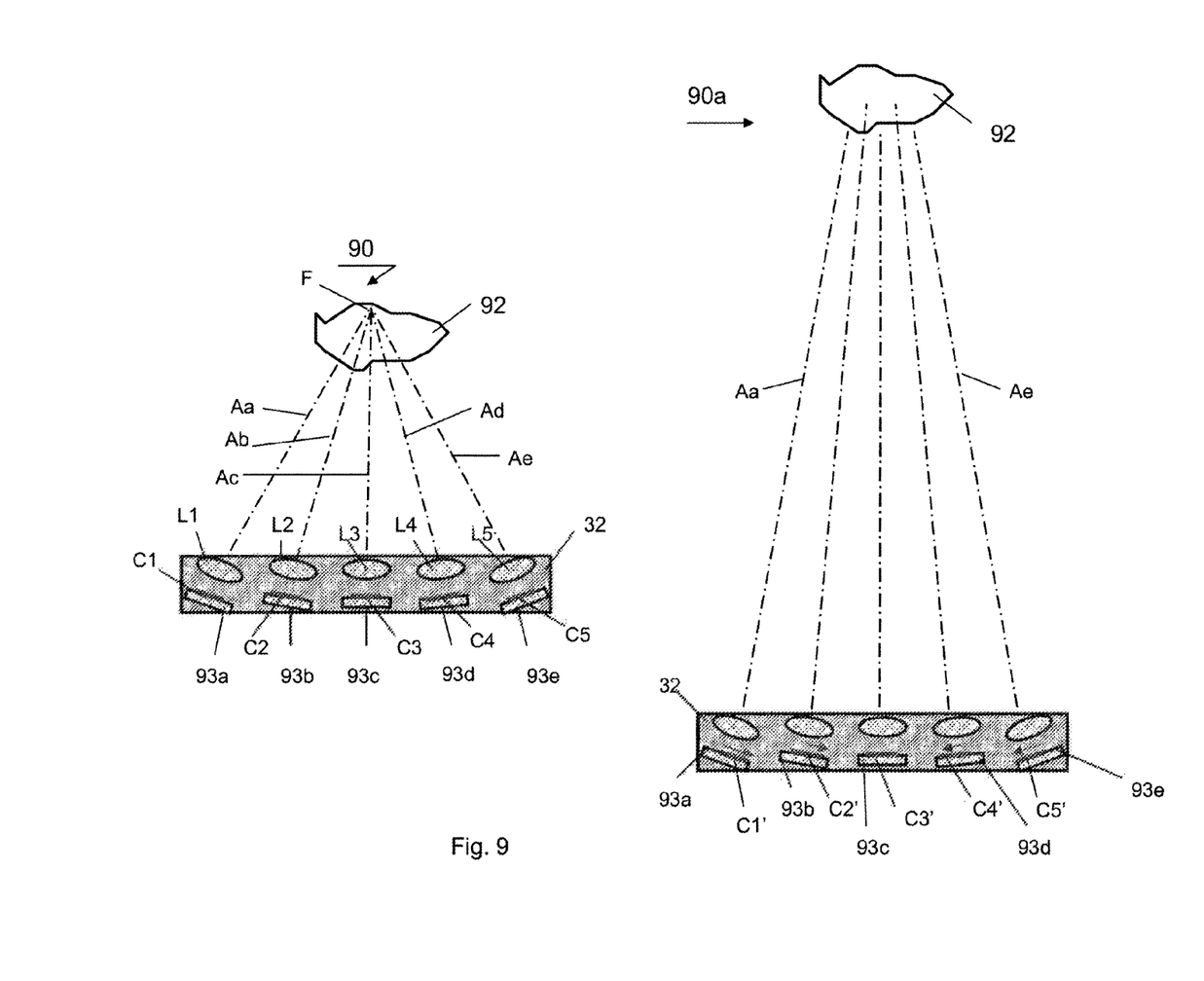
FIG. 9 provides a schematic view of an embodiment of viewing control in a system according to the invention.

FIG. 9 provides a schematic view of an embodiment of viewing control in a system according to the invention. In this figure, in view 90, for clarity purposes, only a portion 32 of a tool is depicted, wherein a set of camera chips 93a, 93b, 93c, 93d, 93e is provided. In order to avoid image degradation due to internal light scattering at least in the portion 32, the camera chips 93a, 93b, 93c, 93d, 93e may be separated by a suitable light barrier, similar to the light barrier discussed with reference to FIG. 6. In this embodiment, the individual camera chips 93a, 93b, 93c, 93d, 93e are provided with corresponding lenses L1, L2, L3, L4, L5, which can be at least rotated together with the camera chips. It will be appreciated that an individual rotation as well as collective rotation is contemplated. Individual rotation may be advantageous for purposes of adjusting a distance to a focus F. It will be appreciated that the focus F may be arranged either before the object 92, on the object 92 or beyond the object 92. In this was a degree of concentricity of the camera array may be adjusted.

In order to enable such adjustment, the camera chips may be rotated about a suitable axis of rotation (not shown), which may be perpendicular to an individual viewing direction Aa, . . . , Ae. In this case a central portion of respective camera chip C1, C2, C3, C4, C5 may be used for acquiring an image.

Alternatively, or additionally, the camera chips 93a, 93b, 93c, 93d, 93e may be rotated to displace the focus F, for example vertically or horizontally. In this case respective driving means may be actuated simultaneously.

View 90a presents schematically a further embodiment of a system according to the invention, wherein a portion of a camera chip conceived to be used to acquire an image may be adjustable for adjusting a degree of concentricity of the camera array. In this embodiment, when other elements are the same discussed with reference to view 90, each camera chips 93a, 93b, 93c, 93d, 93e is controllable by a suitable soft-ware program (not shown) for selecting a suitable active area of the camera chip for acquiring and/or for providing an image. For example, the concentricity of the camera array may be adjusted by allowing the camera chip 93a to provide an image using a portion C1' of the chip area, the camera chip 93b to use a different portion C2' for acquiring an image, the camera chip 93c to use a still different portion C3' for acquiring an image, the camera chip 93d to use a still different portion C4' for acquiring an image and the camera chip 93d to use a still different portion C5' for acquiring an image. By controlling a position of respective portions the concentricity degree of the camera array may be adjusted. It will be appreciated that although FIG. 9 depicts an embodiment wherein a central camera chip provides a substantially central view on the object 92 an off-axis viewing is contemplated.

While specific embodiments have been described above, it will be appreciated that the invention may be practiced otherwise than as described. It will be appreciated that the three-dimensional environment may comprise an object occluded by a further object. The descriptions above are intended to be illustrative, not limiting. Thus, it will be apparent to one skilled in the art that modifications may be made to the invention as described in the foregoing without departing from the scope of the claims set out below.

What is claimed is:

1. An endoscope system for inspection of a three-dimensional environment by a user, comprising:

an endoscope tool arranged to be introduced in a vicinity of the three-dimensional environment, said endoscope tool comprising at least one camera chip arranged at or near a distal end of the endoscope tool to generate a plurality of images of objects present in the three-dimensional environment, said plurality of images having respective viewpoints;

a display unit arranged to receive at least one image from said plurality of images; and a motion tracking system arranged to determine a viewing position of the user for selecting or for generating an image from the said at least one camera chip for displaying said image on the display, wherein said image has a viewpoint corresponding to the said viewing position, wherein the at least one camera chip is displaceable for generating the plurality of images having respective viewpoints, wherein the at least one camera chip is motorized for enabling displacement with respect to the endoscope tool, and wherein the motion tracking system comprises a head tracking system arranged to generate a trigger signal for causing the at least one camera chip or the camera chips to displace, so that a user may control selection of a suitable image using head motion.

2. A system according to claim 1, wherein the at least one camera chip is arranged on a support, the support being displaceable with respect to the endoscope tool.

3. A system according to claim 1, wherein the motion tracking system is further arranged to control a displacement of the at least one camera chip for generating said image having said viewpoint.

4. A system according to claim 1, wherein the at least one camera chip comprises an array or a matrix of camera chips.

5. A system according to claim 4, comprising a sole camera chip divided into sub-regions, each sub-region being capable of generating an individual image.

6. A system according to claim 4, further comprising a multi-lens structure for cooperating with said sub-regions.

7. A system according to claim 4, further comprising a light barrier for optically separating said camera chips or said sub-regions.

8. A system according to claim 4, wherein the array or the matrix of camera chips is arranged concentrically.

9. A system according to claim 8, wherein the array or a matrix of camera chips is arranged on a concentric line or on a concentric area.

10. A system according to claim 1, further comprising a control unit arranged to select two images of the said plurality of images for displaying a stereoscopic image with parallax on the display for a viewing position of the user, said stereoscopic image corresponding to said viewing position.

* * * * *